United States Patent [19]

Kamienski et al.

[11] 4,006,187
[45] Feb. 1, 1977

[54] PREPARATION OF ARYLLITHIUM COMPOUNDS BY METALATION

[75] Inventors: Conrad W. Kamienski; Robert C. Morrison; Kenneth R. Martin, all of Gastonia, N.C.

[73] Assignee: Lithium Corporation of America, New York, N.Y.

[22] Filed: Oct. 6, 1971

[21] Appl. No.: 187,149

[52] U.S. Cl. .......................... 260/577; 260/612 D; 260/665 R; 252/363.5

[51] Int. Cl.² ...................... C07C 87/52; C07F 1/02

[58] Field of Search ............... 260/577, 665 R, 612

[56] References Cited

UNITED STATES PATENTS

| 3,452,111 | 6/1969 | Kamienski et al. | 260/665 |
| 3,492,369 | 1/1972 | Naylor | 260/879 |
| 3,534,113 | 10/1970 | Eastham et al. | 260/665 |
| 3,663,585 | 5/1972 | Langer | 260/665 X |

Primary Examiner—Robert V. Hines
Attorney, Agent, or Firm—Wallenstein, Spangenberg, Hattis & Strampel

[57] ABSTRACT

Process of metalating benzene containing alkyl, alkoxy or dialkylamino substituents, such as toluene, anisole and N,N-dimethyl-aniline, with an organolithium compound such as sec-butyllithium adducts with styrene, in the presence of a tertiary alkyl amine (containing no methyl groups) such as triethylamine, the ratio of lithium in said organolithium compound to the tertiary alkyl amine being 1 gram atom of the lithium to from about 0.25 to about 4 gram moles of the tertiary alkyl amine.

11 Claims, No Drawings

PREPARATION OF ARYLLITHIUM COMPOUNDS BY METALATION

Our invention relates to improvements in the preparation of certain aryllithium compounds by metalation of certain types of substituted benzenes, metalation occurring on the substituent group or groups.

The lithium metalation of aromatic hydrocarbons has heretofore been known and is disclosed in various publications and patents including, for example, U.S. Pat. No. 3,534,113. Thus, for instance, toluene may be readily metalated to form benzyllithium by slow addition of approximately 3 molar equivalents of tetrahydrofuran (THF) to a toluene solution containing 1 molar equivalent of sec-butyllithium at −15° C. Should less than this amount of THF be employed, however, partial precipitation of a benzyllithium-THF complex occurs, resulting in an undesirable mixture of product in both solid and solution form. Moreover, the use of THF tends to promote side reactions, particularly under certain temperature conditions, due to its cleavage both by the sec-butyllithium and by the benzyllithium. Another difficulty is the control of reaction temperature during the metalation, e.g., a sudden increase of about 15° C occurs after addition of ¾ of the THF in the above example.

It has been discovered that substitution of THF in the above metalation with certain tertiary alkylamines hereafter described, notably triethylamine (TEA), markedly improves the process and product characteristics. All of the TEA may be added at the start of the metalation along with the alkyllithium compound and the substituted benzene compound to be metalated. Only 1 to 2 molar equivalents of TEA based on sec-butyllithium are required. The reaction proceeds easily and smoothly at ambient temperature with no sudden heat surges. All of the benzyllithium product is soluble in toluene at either the 1- or 2- molar equivalent TEA level. In addition, no cleavage of TEA occurs either during or after the reaction. Thus, a highly stable solution of benzyllithium is formed by this process, which has, so far as we are aware, hitherto been unavailable by any other means. For instance, it is known that benzyllithium is not soluble in the absence of ethereal or tertiary amine solvents. In addition, as has been stated above, ethereal solvents are not preferred either because insoluble complexes form at low ether concentrations or because side reactions due to ether cleavage occur at higher ether concentrations.

Ethers, and tertiary amines bearing methyl substituents except as noted below, should be avoided in environments where organolithium compounds (such as benzyllithium) are used as anionic polymerization catalysts for conjugated dienes since, in their presence, the resulting polydienes possess microstructures significantly higher in 1,2- or vinyl linkages than do those polydienes prepared with organolithium compounds containing no admixed ether or such tertiary amines bearing methyl constituents.

It has also been found, in accordance with the present invention, that adducts of alkyllithium compounds such as sec-butyllithium, with vinyl-substituted aromatic compounds such as styrene, metalate certain substituent groups of substituted benzene compounds namely, those containing alkoxy and dialkylamino substituents, in the presence of tertiary alkyl amines containing no methyl groups. Thus, by way of illustration, 1-lithio-3-methylpentylbenzene, an adduct formed by reaction of styrene with sec-butyllithium in the presence of TEA, metalates anisole substantially quantitatively to ortho-anisyllithium. Toluene, too, is effectively metalated by this adduct to form benayllithium. Thus, typical organolithium compounds useful as metalating agents in conjunction with such tertiary alkyl amines as TEA are adducts of alkyllithium compounds with vinylaromatic compounds, such as 1-lithio-3-methylpentylbenzene; 1-lithio-5-methylheptene-2; 1-lithio-3,3-dimethylbutylbenzene; 1,3-bis-(1-lithio-3-methylpentyl)benzene; 3(1-lithio-3-methylpentyl) toluene; and 3,5-dimethyl(1-lithio-3-methylpentyl) benzene. Adducts of alkyllithium compounds and conjugated dienes, such as 1,3-butadiene and isoprene, can also be used effectively as metalating agents, illustrative examples of such adducts being 1-lithio-5-methylheptene-2 and 1-lithio-2,5-dimethylheptene-2.

Where the adducts of the alkyllithiums or cycloalkyllithiums with vinyl-substituted aromatic compounds are used as the metalating agents, the vinyl-substituted aromatic compounds utilized in preparing said adducts can be selected from a large group illustrative examples of which are sytrene, alpha-methylstryrene; vinyltoluene; 1-vinylnaphthalene; 2-vinylnaphthalene; 1-alpha-methylvinylnaphthalene; 2-alpha-methylvinylnaphthalene; 1,2-diphenyl-4-methylhexene-1; 1,6-diphenylhexadiene-1,5; 1,3-divinylbenzene; 1,3,5-trivinylbenzene; 1,3,5-triisopropenylbenzene; 1,4-divinylbenzene; 1,3-distyrylbenzene; 1,4-distyrylbenzene; 1,2-distyrylbenzene; and mixtures of these; and also alkyl, cycloalkyl, aryl, alkaryl and aralkyl derivatives thereof in which the total number of carbon atoms in the combined hydrocarbon constituents is generally not greater than 12, examples of which compounds include 3-methylstyrene; 3,5-diethylstyrene; 2-ethyl-4-benzylstyrene; 4-phenylstyrene; 4-p-tolylstyrene; 2,4-divinyltoluene; 4,5-dimethyl-1-vinylnaphthalene; 2,4,6trivinyltoluene; and 2,4,6-triisopropenyltoluene. Reference is made to U.S. Pat. No. 3,377,404 for disclosures of additional vinyl-substituted aromatic compounds which are incorporated herein by reference. Styrene is particularly satisfactory. The adducts are readily made as, for instance, by adding styrene to a solution of sec-butyllithium in hexane containing an equivalent of TEA at 0° C.

Metalations with these systems are best carried out at temperatures in the range of about 0° to about 50° C, with an especially desired temperature range being +20° to +30° C, i.e., generally speaking, ambient temperature.

Generally, the proportion of TEA, or other tertiary alkyl amine or trialkylamine, to alkyllithium, such as sec-butyllithium, will be in the range of from about 0.25 to 4 molar equivalents per equivalent of alkyllithium compound in the metalating adduct, a most desirable range being from 1 to 2 molar equivalents of TEA, or other said amine, per equivalent or alkyllithium.

The aforesaid alkyl tertiary alkyl amines or trialkylamines used in the practice of the present invention, as stated above, are those containing no methyl substituents, and are exemplified, in addition to TEA, by diethyl-n-propylamine, diethyl-isopropylamine; ethyl-di-n-propylamine; ethyl-diisopropylamine; tri-n-propylamine; tri-isopropylamine; tri-n-butylamine; ethyl-di-n-butylamine; diethyl-n-butylamine; ethyl-diisobutylamine; ethyl-diamylamine; ethyl-n-butyloctylamine, and the like. While, where the tertiary alkyl amines are alkyl tertiary amines no methyl substituents should be attached to the nitrogen atom, if the nitrogen atom is attached to an aromatic or aryl group, then a methyl group or groups may be present as, for instance, in the case of dimethyl aniline or methyl-ethyl aniline. Generally, however, and, of course, where the tertiary amine is aliphatic, the alkyl groups will contain from 2 to 12 carbon atoms and will advantageously be normally liquid, that is, liquid at room or ambient temperatures. TEA is especially advantageous.

The solvents for these metalation reactions are generally saturated hydrocarbons, e.g., alkanes and cycloalkanes, such as n-hexane, n-heptane or cyclohexane, but they may also consist either solely of the substrate to be metalated, such as, for example, toluene or meta-xylene or mixtures thereof with saturated hydrocarbons. Benzene is a less desirable solvent since it is also metalated, although at a much slower rate. Generally, metalations proceed much more rapidly when the substrate to be metalated is also the solvent.

The substituted benzenes which are metalated in accordance with the present invention are those in which the substituents on the benzene ring are one or more alkyl, alkoxy or dialkylamino groups. Generally, the number of such substituent groups should not exceed three, and the number of carbon atoms in each alkyl group or alkoxy group should not exceed 6 and, more desirably, should not exceed 4, typical of said alkyl groups being methyl, ethyl, propyl, isopropyl, butyl, isobutyl, amyl and hexyl and their corresponding alkoxy groups. Illustrative of said substituted benzene compounds are toluene, m-xylene, p-xylene, pseudocumene, mesitylene, durene, ethylbenzene, diethylbenzene, n-propylbenzene, isopropylbenzene, n-butylbenzene, isobutylbenzene, and the like; anisole; 1,3-dimethoxybenzene; N,N-dimethylaniline, and 1,3-bis-(N,N-dimethylamino)benzene.

The organolithium compounds which are utilized in the practice of the process of the present invention are the adducts of $C_2$–$C_{12}$ alkyllithiums as well as cycloalkyllithiums with said vinyl-substituted aromatic compounds. These include, by way of example, said adducts utilizing ethyllithium, n-propyllithium, isopropyllithium, n-butyllithium, isobutyllithium, sec-butyllithium, tert-butyllithium, n-amyllithium, isoamyllithium, sec-amyllithium, tert-amyllithium, the hexyl-, octyl-, nonyl-, decyl and dodecyllithiums, cyclopentyllithium and cyclohexyllithium. Of particular utility are said adducts with the $C_4$–$C_5$ alkyllithiums, and especially satisfactory is sec-butyllithium.

In view of the foregoing, it will also be understood that di- and poly-metalation can be effected through the practice of the present invention, where there if more than one of the foregoing substituents on the benzene.

The following examples are given, by way of illustration, of practicing the process of our invention. It will be understood that numerous other examples will readily occur to those skilled in the art in light of the novel guiding principles and teachings disclosed herein.

EXAMPLE I

Preparation of Benzyllithium

From 1-lithio-3-methylpentylbenzene

To 200 ml of sec-butyllithium in hexane (2.05 N) at −20° C there is added 57.2 ml of TEA, followed by 47 ml (0.41 moles of styrene diluted with 30 ml of hexane. Then 43.5 ml of toluene (0.41 moles) is added and the resulting solution is placed in a constant temperature bath at 35° C. Aliquots of the solution are removed periodically, treated with excess trimethylchlorosilane in diethyl ether, and analyzed by G.L.C. for 3-methylpentylbenzene, the amount of which hydrocarbon indicating the percentage of toluene metalated. The results are shown in the following tabulation:

| Time (hrs) | % Metalation |
|---|---|
| 24 | 19.5 |
| 46 | 44 |
| 78 | 63 |
| 102 | 76 |

Metalation is essentially complete in 150 hrs. By contrast, n-butyllithium . TEA metalates toluene much more slowly, only about 10% metalation occurring in a period of 156 hrs at 35° C.

EXAMPLE II

Preparation of o-Anisyllithium

From 1-Lithio-3-Methylpentyltoluene

An adduct, 1-lithio-3-methylpentyltoluene, is formed by adding 13.92 g (0.118 moles) of vinyltoluene in 18 ml of hexane to a solution of 200 ml of 1.18 N sec-butyllithium in hexane containing 23.84 g (0.236 moles) of triethylamine at −20° C. After warning to room temperature and after the sec-butyllithium disappears from the deep orange-red solution, 76.5 ml (0.708 moles) of anisole are added. On standing at room temperature overnight, a copious precipitate of o-anisyllithium forms in the bottle and the orange-red color disappears completely. This solid is filtered off, washed with hexane and then with cyclohexane. The cyclohexane wash is found to contain o-anisyllithium by NMR analysis.

We claim:

1. A process for the preparation of aryllithium compounds which consists in metalating (a) an aromatic compound selected from the group consisting of substituted benzenes in which metalation of the substituent is effected and in which the substituents are selected from the group consisting of alkyl, alkoxy and dialkylamino with (b) an adduct of an organolithium compound, selected from the group consisting of $C_2$–$C_{12}$ alkyllithiums and cycloalkyllithiums, with a vinyl-substituted aromatic compound, in the presence of (c) a member selected from the group consisting of tertiary alkyl amines containing no methyl group and aryl tertiary amines in which the nitrogen of said aryl tertiary amine is directly attached to an aromatic radical, the ratio of the lithium in the (b) adduct to the (c) ingredient being in the range of 1 gram atom of lithium to from about 0.25 to about 4.5 gram moles of the (c) ingredient.

2. A process according to 1, wherein the ratio of the lithium in said (b) adduct to the (c) ingredient is 1 gram atom of lithium to 1 to 2 gram moles of the (c) ingredient.

3. A process according to claim 1, wherein the (a) ingredient is toluene.

4. A process according to claim 1, wherein the (b) ingredient is 1-lithio-3-methylpentylbenzene.

5. A process according to claim 1, wherein the (c) ingredient is triethylamine.

6. A process according to claim 5, wherein the (a) ingredient is a $C_1$–$C_4$ alkoxy benzene, and the (b) adduct is an adduct of a vinyl-substituted aromatic compound with a member selected from the group consisting of secondary and tertiary $C_4$–$C_5$ alkyllithiums.

7. A process according to claim 6, wherein the (a) ingredient is anisole.

8. A process according to claim 6, wherein the (b) ingredient is 1-lithio-3-methylpentylbenzene.

9. A process according to claim 4, wherein the (a) ingredient is a dialkylaminobenzene in which each of the alkyl groups contains from 1 to 4 carbon atoms, and the (b) adduct is an adduct of a vinyl-substituted aromatic compound with a member selected from the group consisting of secondary and tertiary $C_4$–$C_8$ alkyllithiums.

10. A process according to claim 9, wherein the (a) ingredient is N,N-dimethyl-aniline.

11. A process according to claim 9, wherein the (b) ingredient is 1-lithio-3-methylpentylbenzene.

* * * * *